United States Patent [19]

Armour et al.

[11] Patent Number: 4,994,558

[45] Date of Patent: Feb. 19, 1991

[54] IMMUNOGLOBULIN CONJUGATES

[75] Inventors: Henry K. Armour, Indianapolis, Ind.; G. Davon Kennedy, Atlanta, Ga.; Gary A. Koppel; William L. Scott, both of Indianapolis, Ind.

[73] Assignee: Eli Lilly and Company, Indianapolis, Ind.

[21] Appl. No.: 294,338

[22] Filed: Jan. 9, 1989

Related U.S. Application Data

[60] Division of Ser. No. 124,191, Nov. 23, 1987, Pat. No. 4,814,438, Continuation-in-part of Ser. No. 946,351, Dec. 24, 1986.

[51] Int. Cl.$^5$ .................... C07K 17/06; A61K 39/44; A61K 31/70
[52] U.S. Cl. .................................. 530/391; 530/389; 424/85.91; 536/23
[58] Field of Search ................... 424/85.91; 530/389, 530/391; 536/23

[56] References Cited

U.S. PATENT DOCUMENTS

| 4,340,728 | 7/1982 | Endo et al. | 536/23 |
|---|---|---|---|
| 4,526,988 | 7/1985 | Hertel | 549/313 |
| 4,650,675 | 3/1987 | Borel et al. | 424/85.8 |
| 4,692,434 | 9/1987 | Hertel | 549/313 |
| 4,816,569 | 3/1989 | Miyoshi | 536/29 |
| 4,845,200 | 7/1989 | Cullinan et al. | 530/391 |

FOREIGN PATENT DOCUMENTS

| 88695 | 9/1983 | European Pat. Off. | |
| 0184365 | 6/1986 | European Pat. Off. | 536/23 |
| 1446536 | 8/1976 | United Kingdom | 530/389 |
| 1523980 | 9/1978 | United Kingdom | |
| 2137210 | 10/1984 | United Kingdom | |

OTHER PUBLICATIONS

Heinemann, V. et al. (1988) Cancer Res. 48:4204–4031.
Blair, et al., "Linkage of Cytotoxic Agents to Immunoglobulins," *J. Immunological Methods*, 59, 129 (1983).
Ghose, et al., "Preparation of Antibody-Linked Cytotoxic Agents," *Methods Enzymology*, 93, 280 (1983).
Hurwitz et al., *J. Med. Chem.* 28, 137-40 (1985).
Halmos et al., *Carbohydrate Res.* 156, 256-63 (1986).
Hurwitz, *Biopolymers*, 22, 557-67 (1983).

Primary Examiner—Margaret Moskowitz
Assistant Examiner—Kay K. Kim
Attorney, Agent, or Firm—Joseph A. Jones; Leroy Whitaker

[57] ABSTRACT

Immunoglobulin conjugates formed by reacting a difluoronucleoside with an immunoglobulin via an alkane dioic acid linking group.

12 Claims, No Drawings

IMMUNOGLOBULIN CONJUGATES

CROSS-REFERENCE

This application is a division of application Ser. No. 07/124,191, filed Nov. 23, 1987, now U.S. Pat. No. 4,814,438, which is a continuation-in-part of copending application Ser. No. 06/946,351, filed Dec. 24, 1986.

BACKGROUND OF THE INVENTION

Despite the development of numerous chemical agents and sophisticated regimens of drug therapy, the ravages of cancer continue to extract an ever-increasing human toll of suffering and death. Although many advances have been made, especially in the area of combination drug therapy, the need for new and better methods of treating neoplasms and leukemias has not diminished. This is especially evident in the area of inoperable or metastatic solid tumors, such as various forms of lung cancer.

While the treatment of cancer was once considered impossible, great strides have been made during the past ten years in controlling the ravages of this often fatal disease. Several drugs which contribute to the increasing rate of survival are now routinely used clinically. The most commonly employed antitumor agents include methotrexate, doxorubicin and vinca alkaloids such as vincristine. However, research continues in an attempt to develop more effective compounds with greater safety. This invention provides valuable improvements in the treatment of tumors.

EPO Patent Application Publication No. 184,365 describes the use of certain difluoronucleosides for the treatment of neoplasms in mammals. The antiviral use of some of these same nucleosides and methods for their preparation are disclosed in U.S. Pat. No. 4,526,988 and British Patent Application No. GB 2172287. These compounds were found to have useful activity against a variety of tumor systems in mice.

The present invention provides immunoglobulin conjugates of some of these difluoronucleosides. Although the general concept of conjugating drugs to antibodies is generally known, e.g., EPO Patent Application No. 88695, the literature clearly acknowledges the manner and means for which conjugation is accomplished can be critical to obtaining conjugates having useful biological properties. For example, where a compound or drug has more than one reactive functional group, attachment through one functionality may provide a conjugate with significantly greater or lesser biological activity as compared with conjugation through a different functional group. Similarly, the manner in which such conjugation occurs is often critical to the biological utility. In some instances, better biological activity is obtained by covalently linking the compound and antibody directly whereas in other cases a linking group of some type between the two moieties is preferred. Thus, in most cases, there is no way of predicting whether a particular manner of conjugation will provide a useful conjugate.

SUMMARY OF THE INVENTION

The present invention provides immunoglobulin conjugates of the general formula $(Q)_n$-Im where Im is an immunoglobulin or immunoglobulin fragment, n is about 1-10, and Q is an acylated difluoronucleoside of the formula

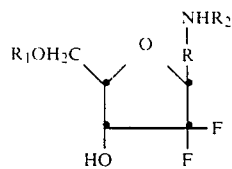

wherein the —R—NH— moiety is

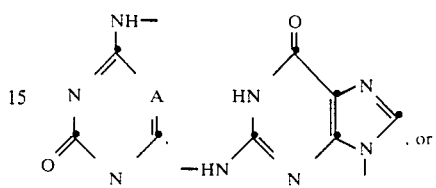

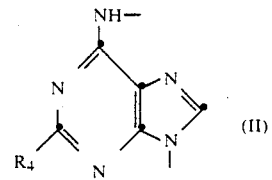

$R_1$ is hydrogen, $C_1$-$C_4$ alkyl, —$COR_3$, or —COXCO—; $R_2$ is hydrogen or —COXCO—; $R_4$ is hydrogen, $C_1$-$C_4$ alkyl, amino, bromo, fluoro, chloro, or iodo; $R_3$ is hydrogen or $C_1$-$C_4$ alkyl; X is a bond, $C_1$-$C_{10}$ straight chain alkylene, $C_2$-$C_{10}$ branched alkylene, $C_2$-$C_{10}$ alkenylene, $C_3$-$C_{10}$ alkynylene, $C_3$-$C_6$ cycloalkylene, phenylene, or hydroxysubstituted $C_1$-$C_{10}$ alkylene, and A is N or C—$R_4$; provided that one and only one of $R_1$ and $R_2$ is —COXCO—.

Also provided by this invention are intermediates of the formula Q—OH, i.e., compounds of the formula

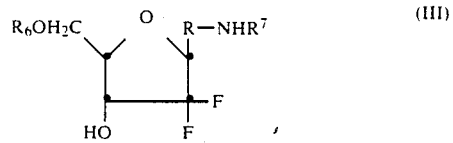

wherein $R_6$ is hydrogen, $C_1$-$C_4$ alkyl, —$COR_3$ or —COXCOOH; $R_7$ is hydrogen or —COXCOOH; provided that one and only one of $R_6$ and $R_7$ is —COXCOOH.

Compounds of formula III are useful as intermediates to the conjugates of this invention, and also possess useful antitumor activity.

DETAILED DESCRIPTION AND PREFERRED EMBODIMENTS

This invention provides conjugates formed by the reaction of an acid of formula (III) in activated form with one or more amino groups of the immunoglobulin molecule, for example, amino groups derived from lysine residues.

Preferred conjugates are those wherein $R_1$ is hydrogen and —R—NH— is a 4-amino-2-oxo-1-pyrimidinyl radical. Preferred X groups are alkylene moieties, particularly those containing 2-4 carbon atoms. Further preferred conjugates are those wherein $R_2$ is hydrogen and $R_1$ is —COXCO—; and those wherein n is about 4–8.

Preferred intermediates are those of formula III wherein $R_6$ is —COXCOOH.

It is recognized that the difluoro ribosides of formulas I and III can exist either in the α- or β- form. This invention provides for conjugates having ribosides in either the racemic, or individual α- or preferred β- forms.

The acids of formula III are prepared from the nucleosides of formula IV

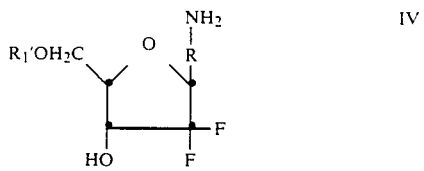

wherein $R_1'$ has the meanings of $R_1$ other than —COXCO—, by standard techniques. Of course, $R_1'$ must be hydrogen if the linking group is to be placed on the 5'-methanol.

In general, the linking group is put in place by allowing an amine of formula IV to react with the mono activated diacid of the formula ZCOXCOOH (V). The moiety Z is a carboxy activating group such as those well known in the chemical art and in particular those used in peptide chemistry. Such groups are discussed, for example, in peptide synthesis by M. Bodanszky, et al., 2nd Edition, (1976) John Wiley & Sons, notably pages 85–136. Such values of Z, therefore, include an azide group (—$N_3$), a halo group, for example bromo and especially chloro, an acyloxy group of the formula $R_5COO$ where $R_5$ is an aliphatic or aromatic residue such as $C_1$–$C_4$ alkyl, an alkoxy group, preferably $C_1$–$C_3$ alkoxy or an aryloxy group, a methanesulfonyloxy, tosyloxy, or benzenesulfonyloxy group, an imidazolyl radical, or the residue of an N-acyl hydroxylamine derivative, for example where Z is succinimidoxy, phthalimidoxy or benzotriazolyloxy. Alternatively, a cyclic anhydride of formula VI may be employed in place of V.

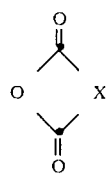

Such chemistry is well known in the art, for example, for acylating alcohol moieties on a molecule, see, e.g., U.S. Pat. No. 4,596,676 and British Patent Application No. 2,137,210. In general, compounds IV and V (or VI) are preferably reacted in a non-reactive solvent such as ethers, for example tetrahydrofuran, diethyl ether, dioxane, and the like, ketones, such as acetone, methyl ethyl ketone, and the like, hydrocarbons, such as hexane, cyclohexane, toluene, and the like, or chlorinated hydrocarbons, such as methylene chloride. Alternatively, or in addition to the solvents, the reaction may be performed in or in the presence of a non-reactive acid scavenger such as pyridine, triethylamine, and the like. It is advisable to use a substantial excess of the reagent of formula V or VI, particularly when the desired product has the linking group on the 5'-methanol. Excess amounts in the range of 2×–6×, particularly about 4×, are desirable.

Reaction of the nucleoside of formula IV with the acylating reagent produces a mixture of products. The amino group is most readily acylated, but the 5'-methanol oxygen and the 3'-hydroxy oxygen are also reactive. Thus, not only monoacylated products but also bis- and tris-acylated products are formed. The various products are separated by chromatographic techniques which are shown in detail in the examples below.

It is believed that the linking group on the 5'-methanol is the most stable of the three acylatable positions. Accordingly, the intermediate of formula III wherein $R_6$ is —COXCOOH can be isolated in quite pure form by cleaving any unwanted acyl groups from the amino nitrogen and the 3'-hydroxy oxygen, as by simple exposure of an aqueous solution to heat. Such isolations are also shown below in the examples.

The thus formed compounds III can then be reacted with the chosen immunoglobulin. The conjugation is accomplished by first activating the acid group of III with a Z functionality as previously described. Again, such methods of preparing acid halides, azides, activated esters, mixed anhydrides, and the like are well known in the art. Of particular importance are activating groups such as succinimidoxy and acid halide, especially acid chloride, derivatives. These activated acids are prepared by standard techniques well known in the art and are then used for coupling with the immunoglobulin. The reaction of the immunoglobulin and the activated form of III is best employed in aqueous medium and at a temperature of about 5–25° C. and a pH of about 7–10. The process results in the attachment by covalent linkage of one or more of the modified difluoronucleosides through the acid groups to form amides with the free amino groups of the immunoglobulin molecule. The number of residues attached will depend on the concentration of the reactants, the duration of the reaction, and the particular immunoglobulin, but the average number is usually approximately 1–10.

In carrying out the conjugation of activated III and the immunoglobulin, a suitable solvent such as dimethylformamide is used as a vehicle to introduce the activated acid into a buffered solution of immunoglobulin in, for example, 0.34M borate buffer at pH 8.6. The conjugate is isolated by gel filtration with a phosphate buffered saline at pH 7.4 as the solvent. Alternatively, the conjugate can be stored in a refrigerator at 4° C. or frozen at, for example, −20° C.

The nucleosides of formula IV are known in the art. U.S. Pat. No. 4,526,988, British Patent Application No. GB 2172287, and EPO Patent Application No. 184,365 are expressly incorporated into this application as illustrative of the compounds which are represented by formula IV and as providing methods for their preparation. Reagents V and VI are either commercially available, known in the literature, or can be prepared by methods known in the art.

The other component for the novel conjugates is an immunoglobulin and, of that class, preferably a monoclonal antibody (MoAb), which is a gammaglobulin such as an IgG or an IgM. The preferred class of immunoglobulins are those which are reactive with antigens on the surface of unwanted cells; i.e., are able to recognize antigens; have antigen recognizing properties.

Techniques for the production of such immunoglobulins from the serum of immunized animals or by culturing hybridomas secreting monoclonal products are well known. The preferred type of antibody for use in the invention is an immunoglobulin which is a gamma-globulin. IgG, IgA, IgE, and IgM subclasses are particularly preferred. Some representative immunoglobulins are as follows, mono- or polyclonal antibodies to
(i) human or animal tumor associated antigens;
(ii) human B- and T-cell antigens;
(iii) human Ia antigens;
(iv) viral, fungal and bacterial antigens; and
(v) cells involved in human inflammatory or allergic reactions.

Of the preferred antibodies to human or animal tumor associated antigens there may be mentioned:
(i) Ig from goats or sheep immunized with carcinoembryonic antigen;
(ii) Ig from rabbit antiacute lymphoblastic leukemia serum;
(iii) Ig from various primate antisera raised against acute lymphoblastic leukemia, acute myeloblastic leukemia, chronic lymphoblastic leukemia and chronic granulocytic leukemia;
(iv) Ig from goats or sheep immunized with lung carcinoma cells, or cellular fractions;
(v) monoclonal Ig from mouse hybridomas secreting anti-human colorectal carcinoma antibodies;
(vi) monoclonal Ig from mouse hybridomas secreting anti-human melanoma antibodies;
(vii) monoclonal Ig from mouse hybridomas that secrete antibodies reacting with human leukemia cells;
(viii) monoclonal Ig from mouse hybridomas secreting antibodies reacting with human neuroblastoma cells;
(ix) monoclonal Ig from mouse hybridomas secreting antibodies reacting with human breast cancer antigens;
(x) monoclonal Ig from mouse hybridomas secreting antibodies reacting with human ovarian carcinoma cells;
(xi) monoclonal Ig from mouse hybridomas secreting antibodies reacting with human osteosarcoma cells, with human pancreatic carcinoma cells, with human prostatic carcinoma cells etc.;
(xii) monoclonal Ig from mouse hybridomas secreting antibodies to adenocarcinomas including lung, renal, breast and pancreas;
(xiii) monoclonal Ig from mouse hybridomas secreting antibodies reacting with human squamous carcinoma cells;
(xiv) monoclonal Ig from human hybridomas (hybridomas which secrete antibodies to the human tumor-associated antigen including, but not limited to, those monoclonals above);
(xv) any antibody or fragment thereof that contains carbohydrate in either the light or heavy chain;
(xvi) Monoclonal Ig from rat, hamster, or other mammalian species not specifically mentioned above, from hybridomas which secrete antibodies to human tumor associated antigens including, but not limited to, those mentioned above.

As indicated above, the conjugate can also be made with immunoglobulin fragments Ig', referred to also as Fab, Fab', F(ab')$_2$ and IgM monomer derived from an antibody by, for example, proteolytic enzyme digestion or reductive alkylation. Useful conjugates are also made with chimeric monoclonal antibodies and bifunctional antibodies. Such materials and methods of preparation are well known and it may be mentioned that preferred proteolytic enzymes are pepsin and papain. See generally Parham, J. Immunology, 131, 2895 (1983); Lamoyi et al., J. Immunological Methods, 56, 235 (1983); Parham, id., 53, 133 (1982); and Matthew et al., id., 50, 239 (1982).

Specific MoAbs exist that are reactive against various tumors; such immunoglobulins which recognize antigens on the surface of, or otherwise associated with tumor cells, include but are not limited to the following:

TABLE I

| Tumor | MoAb | Reference |
|---|---|---|
| Lung | KS1/4 | N. m. Varki, et al., Cancer Res. 44:681, 1984 |
| | 534.F8;604A9 | F. Cuttitta, et al., in: G. L. Wright (ed) Monoclonal Antibodies and Cancer, Marcel Dekker, Inc., N.Y., p. 161, 1984. |
| Squamous Lung Cancer | G1, LuCa2, LuCa3, LuCa4 | Kyoizumi et al., Cancer Res., 45:3274, 1985 |
| | PF 1/D | Fernstein, et al., Cancer Res., 46:2970, 1986 |
| | L1-KS, L2-KS and L4-KS | Starling, et al., Second Int'l. Conf. on Monoclonal Antibody Immunoconjugates for Cancer, San Diego, Mar. 12–14, 1987 |
| Small Cell Lung Cancer | TFS-2 | Okabe et al., Cancer Res. 45:1930, 1985 |
| Colon | 11.285.14 14.95.55 | G. Rowland, et al., Cancer Immunol. Immunother., 19:1, 1985. |
| | NS-3a-22,NS-10 NS-19-9,NS-33a NS-52a,17-1A | Z. Steplewski, et al., Cancer Res., 41:2723, 1981. |
| Melanoma | 9.2.27 | T. F. Bumol and R. A. Reisfeld, Proc. Natl. Acad. Sci. (USA), 79:1245, 1982 |
| | p97 | K. E. Hellstrom, et al., Monoclonal Antibodies and Cancer, loc. cit. p. 31. |
| | R24 | W. G. Dippold, et al., Proc. Natl. Acad. Sci. (USA), 77:6114, 1980. |
| Neuroblastoma | P1 153/3 | R. H. Kennet and F. Gilbert, Science, 203:1120, 1979. |
| | MIN 1 | J. T. Kemshead in Monoclonal Antibodies and Cancer, loc. cit. p. 49. |
| | UJ13A | Goldman et al., Pediatrics, 105:252, 1984. |
| Glioma | BF7,GE2,CG12 | N. de Tribolet, et al., in Monoclonal Antibodies and Cancer, loc. cit. p. 81. |
| Breast | B6.2,B72.3 | D. Colcher, et al., in Monoclonal Antibodies and Cancer, loc. cit. p. 121. |
| Osteogenic Sarcoma | 791T/48, 791T/36 | M. J. Embleton, ibid, p. 181 |
| Leukemia | CALL 2 | C. T. Teng, et al., Lancet, 1:01, 1982. |
| | anti-idiotype | R. A. Miller, et al., |

TABLE I-continued

| Tumor | MoAb | Reference |
|---|---|---|
| Ovary | OC 125 | N. Eng. J. Med., 306:517, 1982. R. C. Bast, et al., J. Clin. Invest., 68:1331, 1981. |
| Prostate | D83.21, P6.2, Turp-27 | J. J. Starling, et al., in Monoclonal Antibodies and Cancer, loc. cit. p. 253. |
| Renal | A6H, D5D | P. H. Lange, et al., Surgery, 98:143, 1985. |

Preferred conjugates are those prepared from monoclonal antibodies, especially those which recognize human cancer cells such as adenocarcinoma, squamous cell carcinoma, transitional cell carcinoma, melanoma, neuroblastoma, small cell carcinoma, leukemia, lymphoma, and sarcoma.

The following examples are illustrative of the conjugates in intermediates of this invention. These examples are illustrative only and are not intended to limit the invention in any way.

EXAMPLE 1

5'-O-(3-Carboxy-1-oxopropyl)-2'-deoxy-2',2'-difluorocytidine

Dry 2'-deoxy-2',2'-difluorocytidine (311 mg) was added to dry ethanol and brought to reflux. Succinic anhydride (2.5 g) was added in portions over a half hour period and the mixture was refluxed an additional ½ hour. The mixture was concentrated in vacuo and the resulting crude product was placed on a silica gel column and eluted with a step gradient of 5%, 20%, and 50% methanol in methylene chloride. The desired product was isolated in the 50% methanol in methylene chloride wash and contained 148 mg of material. This product was combined with product from a similar experiment providing a total of 253 mg of material. This material was taken up in 8 ml of 0.01M ammonium acetate solution. The pH was adjusted with ammonium hydroxide to 8.6 and the solution placed on a freshly packed mono-Q anion exchange column (Pharmacia Inc., 800 Centennial Avenue, Piscataway, N.J. 08854). Desired fractions were combined, frozen, and lyophilized. The residue was dissolved in distilled water, frozen, and lyophilized several more times, then dissolved in a small amount of methanol and benzene, frozen, and lyophilized providing 60 mg of the desired title product. The proton NMR spectra was consistent with the structure of the desired product:

δ 7.68, doublet, 1H (C6,=CH—N); δ 6.24, triplet, 1H (C1', O—CRH—); δ 6.13, doublet, 1H (C5, C=CH—); δ 4.78, singlet, 4 exchangable protons (—OH, —NH); δ 4.2–4.27, multiplet, 4 protons (sugar protons at C3', C4', C5'); δ 2.60 and 2.73, doublet of triplets, 4 protons (succinate protons —CH$_2$CH$_2$—).

EXAMPLE 2

Conjugation of 5'-O-(3-carboxy-1-oxopropyl)-2'-deoxy-2',2'-difluorocytidine with 007B A 25 mg sample of the product from Example 1 was dissolved in a small volume of benzene and methanol, frozen, and lyophilized a total of three times. The residue was dissolved in 1 ml of dry dimethylformamide and 4 ml of freshly distilled tetrahydrofuran. The mixture was cooled to 4° C. and N-methyl morpholine (151 mcl) in tetrahydrofuran was added. After 10 minutes, a 177 mcl sample of isobutyl chloroformate in tetrahydrofuran was added. After stirring for 20 minutes at 4° C., 248 mcl of N-hydroxysuccinimide were added. Stirring was continued for 20 minutes at 4° C. and for 3 hours at ambient temperature. The solution was concentrated in vacuo and kept under vacuum overnight.

The activated ester prepared in the preceding paragraph (31.7 mg) was dissolved in 4.18 ml of dry dimethylformamide. Antibody 007B was prepared by subcloning the cell line producing the published antibody KS1/4 and selecting variant hybridoma clones which produce only the relevant IgG2a monoclonal antibody of KS1/4, and not the irrelevant IgG1 protein. Such clones were grown in cell culture by conventional methods to produce 007B. Five hundred milligrams of 007B in pH 8.6 borate buffer was placed in a round bottom flask and the solution of activated ester added over a 10 minute period. The reaction was stirred in the dark for 3 hours, adjusted to pH 7.4 with 1N hydrochloric acid, and centrifuged for 10 minutes at 2,000 rpm. The supernate was divided in half and each portion placed on a Bio-gel P-6 column (Bio-Rad Laboratories, 32nd and Griffin Avenue, Richmond, California 94804) with phosphate buffered saline (PBS) at pH 7.4 as the eluant. The conjugate peaks were collected in 3 fractions for each portion. Like fractions were combined from the 2 runs. The combined second fractions were concentrated to 3 ml and diluted with PBS to give a solution with a concentration of 25.44 mg/ml with a total volume of 13.29 ml. The protein recovered was 338 mg and the molar ratio of nucleoside to protein was 4:1. The product was sterilized and used for the following in vivo experiments.

EXAMPLE 3

5'-O-(3-Carboxy-1-oxopropyl)-2'-deoxy-2',2'-difluorocytidine

A 600 mg portion of dry 2'-deoxy-2',2'-difluorocytidine, hydrochloride, was added to 6 ml of dry pyridine, and 804 mg of succinic anhydride was added. The reaction mixture was stirred at ambient temperature for 1.5 hours. The mixture was then concentrated to an oil under vacuum, and the oil was stored overnight in the freezer. It was then allowed to stand at ambient temperature for 4 hours, and was chromatographed over a 500 ml Q-Sepharose column (Pharmacia Inc.). The oil was dissolved in 6 ml of 0.1M ammonium acetate buffer, and was passed over the column, eluting with a gradient buffer which changed from 0.1M to 1.0M ammonium acetate, at pH 8.0 at all times. Analytical chromatography of the mixture on a small mono-Q column showed that bisacylated and tris-acylated products were present, as well as mono-acylated product and a small amount of starting material. The product-containing fractions, amounting to about 200 ml, were placed in a 37° C. bath, for 68 hours. At the end of that time, the tris-acylated product had been decomposed and both mono- and bisacylated products were still present.

The product mixture was then separated by preparative chromatography on a mono-Q column, eluting with the same gradient buffer used above. The fractions containing mono-acylated product were collected, pooled and freeze-dried twice to obtain 508 mg of the desired intermediate product. The product was identified by nuclear magnetic resonance analysis, using D$_2$O as the solvent on a 300 mHz instrument. The characteristic features of the spectrum were δ 6.15, doublet, 1H (C5); 6.25, triplet, 1H (C1'); 7.7, doublet, 1H (C6).

EXAMPLE 4

5'-O-(3-Carboxy-1-oxopropyl)-2'-deoxy-2',2'-difluorocytidine

N-(3-Carboxy-1-oxopropyl)-2'-deoxy-2',2'-difluorocytidin

Two hundred mg of 2'-deoxy-2',2'-difluorocytidine, hydrochloride, was dissolved in 2 ml of pyridine, and then 134 mg of succinic anhydride was added. The mixture was stirred at ambient temperature for 1.25 hours, and was then concentrated under vacuum. The residue was dissolved in dichloromethane/methanol, and the solution was absorbed on 1.5 g of silica gel, which was then slurried in dichloromethane and loaded on a 4 g silica gel column. The column was eluted with a gradient solvent, starting with dichloromethane and ending with methanol. The product-containing fractions were combined and freeze-dried overnight to obtain 255 mg of product mixture. It was dissolved in 3 ml of 0.01M ammonium acetate, and was chromatographed on a 22 ml mono-Q fast flow column (Pharmacia Inc.), eluting with the ammonium acetate gradient buffer which has previously been described. Evaporation of the product-containing fractions gave 81 mg of a mixture of the mono-acylated products named in the heading.

The following nmr features of the two products were observed, using analysis as described in Example 3.

|  | N-acylated | O-acylated |
| --- | --- | --- |
| Triplet, 1H (C1') | δ 6.25 | δ 6.25 |
| Doublet, 1H (C5) | δ 7.4 | δ 6.15 |
| Doublet, 1H (C6) | δ 8.2 | δ 7.7 |

EXAMPLE 5

Activation of
5'-O-(3-Carboxy-1-oxopropyl)-2'-deoxy-2',2'-difluorocytidine

A 23.2 mg portion of the intermediate compound of Example 1 was weighed into a 50 ml flask, and was dissolved in a small amount of methanol. Then a few ml of benzene was added, and the solution was evaporated under vacuum. The dissolution and evaporation was repeated once, to assure that the compound was dry. It was then dissolved in 1.2 ml of dimethylformamide, which had been stored in the presence of molecular sieve to dry it. A 14.7 mg portion of N-hydroxysuccinimide was added, followed by 14.5 mg of dicyclohexylcarbodiimide. The mixture was then stirred overnight at ambient temperature, to obtain the succinimidoxy ester of 5'-O-(3-carboxy-1-oxopropyl)-2'-deoxy-2',2'-difluorocytidine.

EXAMPLE 6

Conjugation with antibody 9.2.27

A 624 μl portion of the active ester solution from Example 5 was added to a vial, and to it was added 100 mg of isolated antibody 9.2.27. The mixture was stirred at ambient temperature for a few hours, and was then stored in the refrigerator for two days. The mixture was then chromatographed over a G-50 size exclusion column (Pharmacia Inc.), eluting with PBS. The product-containing fractions were examined by ultraviolet analysis, observing the maximum at 280 amd the minimum at 251 λ. The ratio of drug to antibody was 3.7 moles of drug per mole of antibody.

EXAMPLE 7

Conjugation with antibody 007B

An activated ester solution was prepared as described in Example 5, but in twice the concentration. A 1.4 ml portion of that solution was added to 500 mg of isolated antibody 007B, and the mixture was stirred at ambient temperature for four hours. It was then centrifuged, and the solid pellet was loaded onto and chromatographed through a G-50 column as described in Example 6 above. Two pools of product-containing fractions were obtained, and were analyzed by ultraviolet, as described in Example 6. Analysis of the two pools showed that 8.9 and 10.2 moles of drug were conjugated to each mole of antibody, respectively.

Anti-Tumor Activity In the P3-UCLA Adenocarcinoma Model

The inhibition of the P3-UCLA adenocarcinoma in female nude mice was determined by standard techniques. Inoculation of the mice was performed on day 0, compounds were dosed intravenously days 2, 4, and 8, and evaluation was made on days 14 or 21. The percent inhibition of tumor growth was determined employing controls receiving vehicle only. Groups of 5 mice were used for each test and control group. The dose for the conjugate is expressed as the calculated mg/kg of parent nucleoside administered. The results from these tests are summarized in Table II.

TABLE II

Inhibition of P3-UCLA Adenocarcinoma in Nude Mice

| Compound of Example | Dose (mg/kg)* | Percent Inhibition | |
| --- | --- | --- | --- |
| | | 14 days | 21 days |
| 1 | 5.0 | 25% | 37% |
| 2 | 5.0 | 86% | 84% |
| | 2.5 | 63% | 62% |
| | 0.5 | 31% | 27% |

*Dose administered intravenously on days 2, 4, and 8. Inoculation of cells on day 0; evaluation on days 14 or 21. Dose for Example 2 calculated as mg/kg of parent nucleoside.

Additional tests of the same type were carried out, with observation of the animals, 14, 21 and 28 days after inoculation. The conjugate of Example 2 was a pooled lot having an average conjugation ratio of 7.8.

| Compound of Example | Dose (mg/kg) | Percent Inhibition | | |
| --- | --- | --- | --- | --- |
| | | 14 days | 21 days | 28 days |
| 1 | 10 | 41 | 36 | 28 |
| | 2.5 | 28 | 18 | 2 |
| | 0.5 | 25 | 7 | 23 |
| 2 | 10 | 97 | 99 | 95 |
| | 5 | 97 | 98 | 94 |
| | 2.5 | 96 | 92 | 85 |
| | 1 | 48 | 38 | 32 |
| | 0.5 | 48 | 16 | 4 |

One of the five mice on the highest rate of Example 1 died, as did three of the five mice on the highest rate of Example 2.

The above test results demonstrate the value of conjugating the nucleoside to a directing antibody. It is obvious from the data that the conjugated drug gives more than twice the inhibition of the tumor, compared to the parent nucleoside, even at lower, nontoxic doses.

In Vitro Affinity Testing

In vitro tests were carried out in an ELISA system to determine the affinity of the antibody portion of the conjugated drug for an antigen to which the unconjugated antibody is bound. The results are presented as the fraction of the antibody present in the sample which binds to the antigen.

| Conjugation Ratio | ELISA Result |
|---|---|
| Antibody 007B | |
| 8.9 | 0.43 |
| 6.6 | 0.42 |
| 2.5 | 0.55 |
| Antibody 9.2.27 | |
| 16.5 | 0.15 |
| 4.9 | 0.26 |
| 0 | 0.65 |

The novel conjugates of the invention are useful in the treatment of cancers and as such are preferably prepared for use in formulations suitable for injection. Thus the invention includes a pharmaceutical formulation, for example an injectable preparation comprising a conjugate of the invention together with a pharmaceutically-acceptable carrier or diluent such as are well known in the art. The formulation is preferably in unit dosage form, each dosage containing, for example, from 0.01 to 10 mg of the active ingredient (in terms of the nucleoside drug moiety).

The novel conjugates are effective over a wide dosage range and dosages per week, for example, for the treatment of adult humans suffering from cancer will normally fall within the range of 0.01 to 10 mg/kg (nucleoside drug moiety), more usually in the range of from 0.03 to 9 mg/kg. However it will be understood that the amount of conjugate actually administered will be determined by a physician in the light of the relevant circumstances, including the condition to be treated and the chosen route of administration.

We claim:

1. A conjugate of the formula $(Q)_n$—Im where Im is an immunoglobulin or immunoglobulin fragment, n is about 1–10, and Q is an acylated difluoronucleoside of the formula

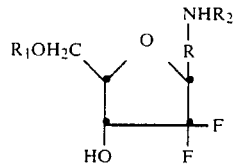

(I)

wherein the —R—NH— moiety is

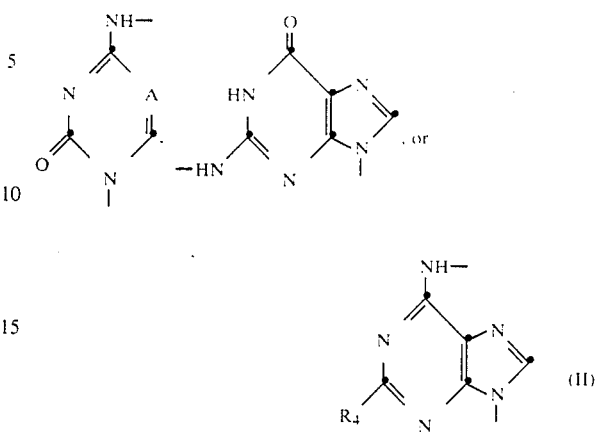

$R_1$ is hydrogen, $C_1$–$C_4$ alkyl, —$COR_3$, or —COXCO—; $R_2$ is hydrogen or —COXCO—; $R_4$ is hydrogen, $C_1$–$C_4$ alkyl, amino, bromo, fluoro, chloro, or iodo; $R_3$ is hydrogen or $C_1$–$C_4$ alkyl; X is a bond, $C_1$–$C_{10}$ straight chain alkylene, $C_2$–$C_{10}$ branched alkylene, $C_2$–$C_{10}$ alkenylene, $C_3$–$C_{10}$ alkynylene, $C_3$–$C_6$ cycloalkylene, phenylene, or hydroxysubstituted $C_1$–$C_{10}$ alkylene, and A is N or C-$R_4$; provided that one and only one of $R_1$ and $R_2$ is —COXCO—.

2. A conjugate of claim 1 wherein $R_2$ is hydrogen.

3. A conjugate of claim 2 wherein —R—NH— is a 4-amino-2-oxo-1-pyrimidinyl radical.

4. A conjugate of claim 3 wherein X is $C_2$–$C_4$ alkylene.

5. A conjugate of claim 4 wherein Q is 5'-O-(1,4-dioxobutyl)-2'-deoxy-2',2'-difluorocytidinyl.

6. A conjugate according to claim 1 in which IM is an immunoglobulin which specifically binds antigen.

7. A conjugate according to claim 6 in which the immunoglobulin is a monoclonal antibody.

8. A conjugate according to claim 7 in which the MoAb recognizes human cancer cells.

9. A conjugate according to claim 8 in which the MoAb recognizes human cancer cells selected from the group consisting of adenocarcinoma, squamous cell carcinoma, transitional cell carcinoma, melanoma, neuroblastoma, small cell carcinoma, leukemia, lymphoma, and sarcoma.

10. A conjugate according to claim 9 wherein Q is 5'-O-(1,4-dioxobutyl)-2'-deoxy-2',2'-difluorocytidinyl.

11. A conjugate according to claim 9 wherein the MoAb is adapted for recognition of human adenocarcinoma cells.

12. A conjugate according to claim 10 wherein the MoAb is adapted for recognition of human adenocarcinoma cells.

* * * * *